United States Patent [19]

Raithaus

[11] Patent Number: 5,840,342
[45] Date of Patent: Nov. 24, 1998

[54] SHARK LIVER EXTRACT FOR STIMULATING THE IMMUNE SYSTEM

[76] Inventor: Lawrence R. Raithaus, P.O. Box 652, Lawai, Kauai, Hi. 96765

[21] Appl. No.: 932,196

[22] Filed: Sep. 17, 1997

[51] Int. Cl.$^6$ .......................... A61K 35/407; A61K 35/12
[52] U.S. Cl. ............................................. 424/553; 424/520
[58] Field of Search ..................................... 424/530, 553, 424/528, 520

[56] References Cited

U.S. PATENT DOCUMENTS 5,451,575  9/1995  Kosuge et al. ........................... 514/182
5,618,925  4/1997  Dupont et al. ........................... 530/400

FOREIGN PATENT DOCUMENTS 360193923  12/1985  Japan .

OTHER PUBLICATIONS

Dunlop et al. "A compartive study of isolutrol versus benzoyl peroxide in the treatment of acne," Australasian J. Dermatol. (1995) 36: 13–15.

*Primary Examiner*—Jean C. Witz
*Assistant Examiner*—Susan Hanley
*Attorney, Agent, or Firm*—Loeb & Loeb LLP; Michael J. Ram

[57] ABSTRACT

A water soluble, non-toxic, purified, biological preparation extracted from sharks liver which inhibits the growth of cancer cells by stimulating the patient's immune system and reduces toxic effects on patients exposed to radiation used to treat cancer. The water soluble material can be administered orally, transrectally, transcutaneously or by direct deposition at a desired spot within the body for reduction or elimination of malignant tumors or for the prevention or reduction of the deleterious effects of radiation treatment on normal cells within the human body. The shark liver extract is produced by grinding the liver, extracting the ground material with water, removing the non-water soluble components and lyophilizing the water soluble components to produce a powdered substance suitable for delivery to the patient, said substance having an extended shelf life.

6 Claims, 3 Drawing Sheets

SHARK LIVER EXTRACT FOR STIMULATING THE IMMUNE SYSTEM

BACKGROUND

The present invention relates to a water soluble, non-toxic, bio-pharmaceutical extracted from sharks liver which stimulates the patient's immune system and which, in turn, inhibits the growth of cancer cells and reduces toxic side effects on patients exposed to radiation used to treat cancer. It is believed the sharks liver extract could also have beneficial effects in conjunction with chemotherapy.

The sharks immune system is different from that of mammals. It does not produce specific antibodies against each microorganism that invades the body. Instead, the shark has a primitive but effective immune system which includes an immunoglobulin molecule (IgM) in the blood circulating through its body. The IgM binds to foreign substances, mainly proteins (antigens), marking those antigens so they can be found and destroyed. This IgM is similar to the IgM which exists in the human fetus but disappears as the fetus matures. "The shark immune system seems to do an extraordinary job of protecting against cancer and other diseases," (*Los Angeles Times*, Aug. 27, 1990, pp B3).

Recent research has suggested that shark cartilage, because of its ability to inhibit blood-vessel growth, may inhibit tumor growth. To this end Carl A. Luer, of Mote Marine Laboratory in Sarasota, Fla., has identified a group of three proteins recovered from shark cartilage which he believes may be suitable for retarding or reversing tumor growth without the harmful side effects of radiation (*Los Angeles Times*, Aug. 27, 1990, pp B3).

Samuel Gruber has reported isolating a protein from a sharks skeleton that, when injected in a tumor, causes the tumor to dry up and die. However, side effects make use of the protein on humans impractical (*San Francisco Chronicle*, Jan. 18, 1989).

Astrid, Johan and Sven Brouhult, and their associates, have reported on the use in cancer patients of preparations, delivered orally in capsules, containing 85% alkoxyglycerol recovered from the oil of the liver of Greenland sharks. When administered prior to radiation, patients with cancer of the uterine cervix showed higher survival rates then if radiation treatment alone is given (*Acta Chem. Scand.* 24, 2 (1970) pp. 730–732); (*Acta Obstet. Gynecol. Scand.* 65(1986) pp. 779–785). Others have taught the alcohol extraction of homogenated shark liver to produce a cytotropic heterogeneous molecular lipid or serum separated from shark blood by alcohol extraction to increase immunity or attack cancer cells.

The materials discussed above are recovered from various organs of the shark using different methods of recovery. They constitute oils or lipids, which are not water soluble. As a result, delivery of the active material, either systemically or directly, to the desired site, or absorption into the target tissue, may be difficult.

There have been reports of a physiological saline extract of shark liver being administered to patients in the former Soviet Republic of Georgia and that material has been used to treat patients with prostate cancer. (Modianova, E. A., Gachechiladze, A. B., Kolotygina, J. M. Kasatkina, N. N., Malenkov, A. B., "Antiblastomogenic and Antipromotor Activity of Katreks," Abstracts of Papers, School Seminar; "Regulation of Tissue Homeostasis: Non-toxic Prophylaxis and Therapy of Chronic Pathologies, Tbilisi, 1987: 191–6; Modianova, E. A., "Predisposition of Epithelial Tissues to the Onset of Spontaneous Tumors as a Manifestation of Impairment of the Resistance of the Integrating Tissue System," In: Ibid 116–118; Glinskii, K. V., Ivanova, A. B., Surgova, T. M., Kaz'min, S. D., Vinnitskii, V. B., "A Study of Several Biochemical Characteristics of the Biopreparation Katreks," In: Ibid:32–41).

However, these materials have several negative characteristics including an unacceptable level of impurities, inconsistency of performance and a limited shelf life of less that about two (2) weeks.

Thus, there is a need for a stable, biologically active, non-toxic material that can be readily isolated and administered to the patient for cancer treatment, which stimulates, enhances, and/or modulates the immune system and reduces or eliminates the toxic side effects of radiation, and possibly, chemotherapy, on patients being treated for various forms of cancer.

SUMMARY

These needs are met by the present invention which comprises a water soluble, lyophilized preparation which can be administered once reconstituted or properly compounded, orally, by intravenous injection, intramuscular, transcutaneously or direct deposition at a desired spot within the body for reduction or elimination of malignant tumors or for the prevention or reduction of the deleterious effects of radiation treatment and possibly of chemotherapy on normal cells within the human body.

More particularly, the invention constitutes a method of recovering, and the products recovered by said method, an extract from the liver of sharks which has significant benefit in stimulating the immune system and reduce the negative side effects of radiation. These materials may also have a beneficial effect when used in conjunction with bone marrow transplants which also necessitate the radiative destruction of the patients diseased bone marrow.

DRAWINGS

These and other features, aspects and advantages of the present invention will become better understood with reference to the following description, appended claims, and accompanying drawings, where:

FIG. 5 is a bar graph showing survival rates responsive to delivery times or protective regimes.

DESCRIPTION

A purified aqueous extract of sharks liver was prepared. It was established that these materials show significant immune stimulation, as reflected by natural killer cell assay, and are more immune stimulating in the same assay than Interferon using C57 BL/6 mice tested Chromium labeled YAC lymphoma cells. Using a mice model at the Division of Radiation Oncology at the National Cancer Institute, we have demonstrated significant and comparable radioprotective effects as stem cell factor (SCF), a known radioprotective substance. Further, the extract prepared as described below, should have beneficial effects when administered to a patient in conjunction with high dose radiation therapy in advanced prostatic carcinoma, and is believed to convey properties of angiogenesis inhibition to tumors and immune stimulation involving NK cell activity properties so as to facilitate the organism's ability to reject cells recognized as "not self" by various methods attributed to NK activity.

METHOD OF PREPARATION

Figure 1:
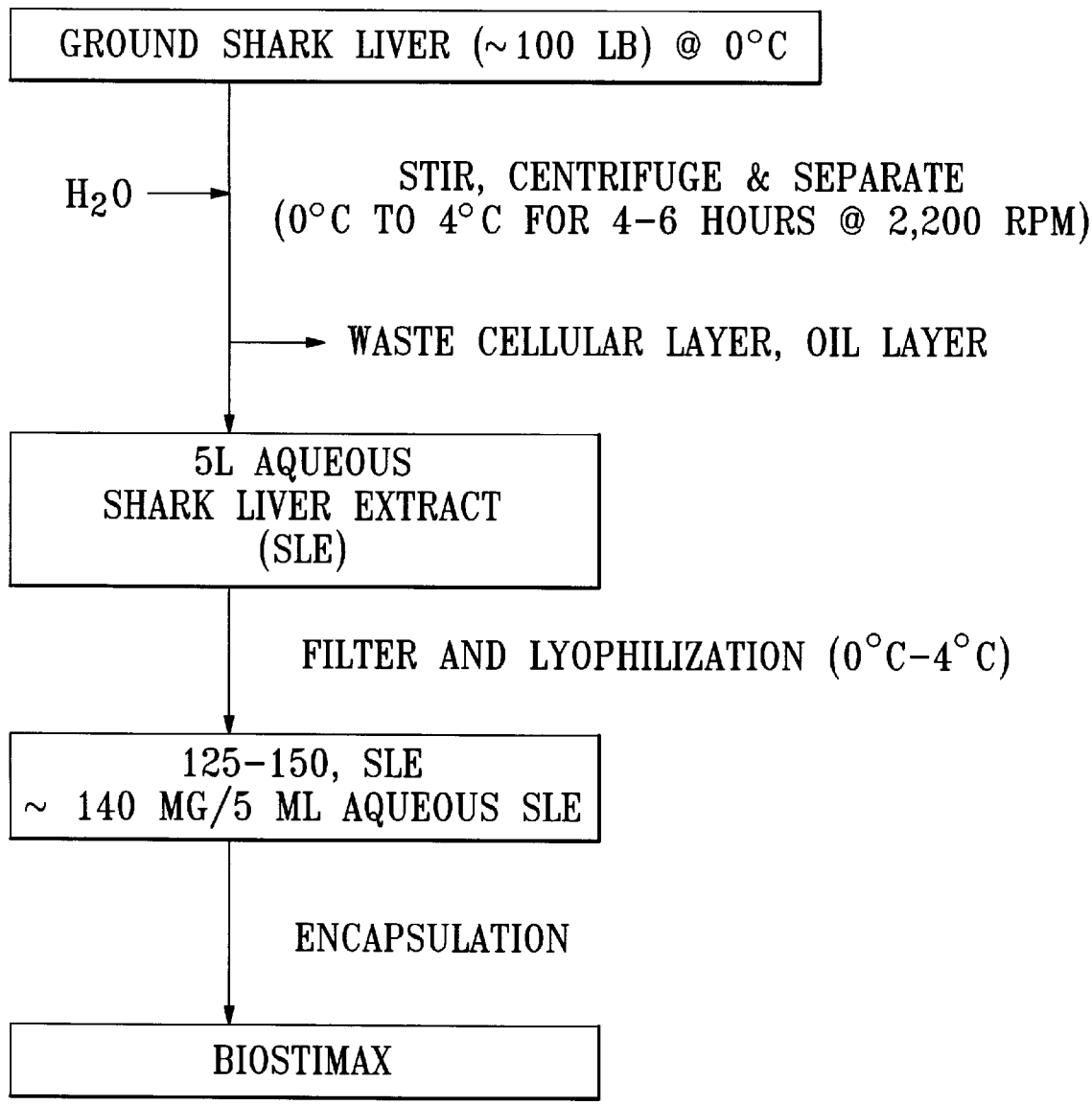
FIG. 1 is a schematic diagram of the process for preparing the liver extract embodying features of the invention.
Figure 2:
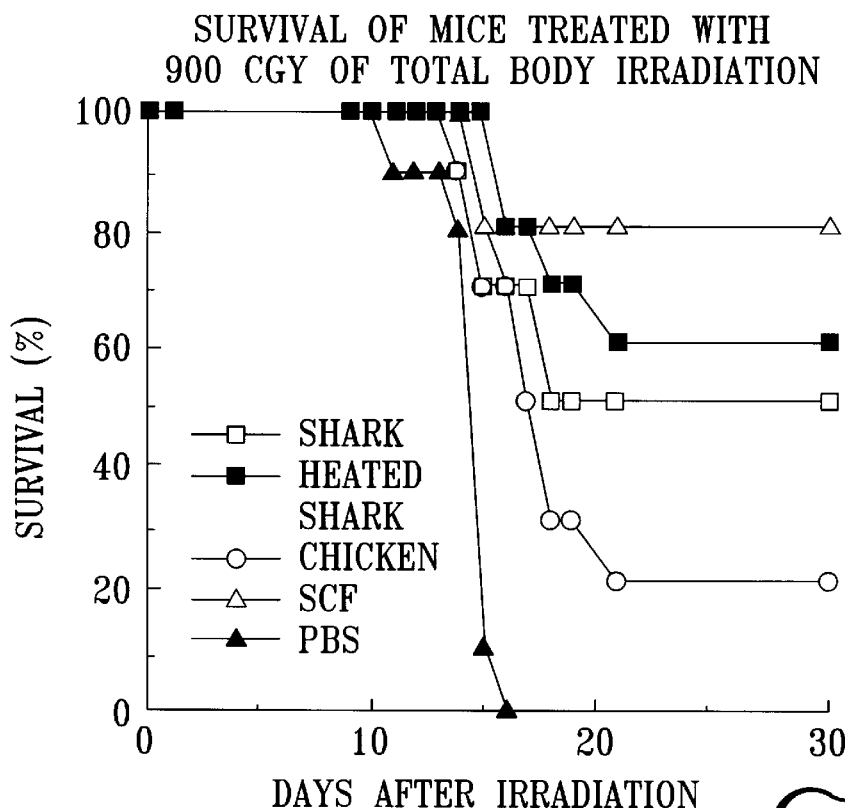
FIG. 2 is a graph showing the survival of mice exposed to 900 cGy irradiation with various protective measures.

FIG. 1 is a schematic diagram showing a method of preparing the shark liver extract. A quantity of shark liver was refrigerated to about 0° C. to 4° C., finely ground, granulated, pulverized, crumbled, milled or otherwise reduced to a powder or slurry to produce subcellular particles of biological material in colloidal suspension and mixed with an equal amount, by weight, of water or physiological saline solution (PSS). Grinding or morselizing was accomplished by processing in a bench top food blender or juicer/processor. The mixture was maintained at 0° C. to 4° C. with stirring and blending for about 20 minutes. Upon spinning the mixture in a centrifuge at 2780 rpm, 0° C. to 4° C. for 6 hours, the mixture separated into three layers comprising a cellular layer, a pink/brown aqueous layer with its water soluble components, and an oil layer. The aqueous layer which contained the desired shark liver extract (SLE) was isolated for further processing. The aqueous layer may be further processed by deaerating, adding more water and centrifuging again to prepare a further purified aqueous layer. The color can be removed by passing the aqueous layer through absorbent materials generally used for that purpose.

The volume of aqueous layer separated out is measured, filtered through a fine filter, preferably a 23μ filter, to remove visible particulate material and generate a clear appearing solution and then flash dried by spraying the liquid into a vacuum chamber at 0° to 4° C. (lyophilization). The resultant powder (lyophilized water soluble SLE) is collected and weighed so that it can be reconstituted to approximately the same volume with a physiologically acceptable diluent for injection. It has generally been found that there is 140 mg of lyophilized material per 5 ml of diluent. Alternatively, the lyophilized material can be encapsulated in an enteric coated gelcap for oral delivery or a suitable material, such as beeswax/glycerol compositions, for forming a body meltable suppository for transrectal or transurethral delivery. The above described process results in a purified, readily administered composition in which the chemical or biological components of shark liver most beneficial for the procedures discussed below are concentrated and non-active materials are removed. The oil layer collected from the centrifuged mixture can also be used in applications previously disclosed for shark liver oil.

In order to demonstrate the efficacy of shark liver extract prepared according to the above described procedures, mice were treated with various materials, all prepared in the same manner. The difference between the material designated "shark" and "heated shark" is that in the heated shark extract was additionally exposed to 100° C. for four (4) minutes following the process set forth above. The figures show the radiation protection effect of Shark Liver Extract before heating (Shark) and after heating (Heated Shark). The controls for comparison are: Stem Cell Factor (SCF), Chicken Liver Extract (Chicken), and Phosphate Buffer Saline (PBS). The chicken liver extract was derived from chicken liver treated in a manner similar to the SLE. The SCF has known radiation protective properties. The Phosphate Buffer is the carrier, which has no known immune or protective properties.

Figure 3:
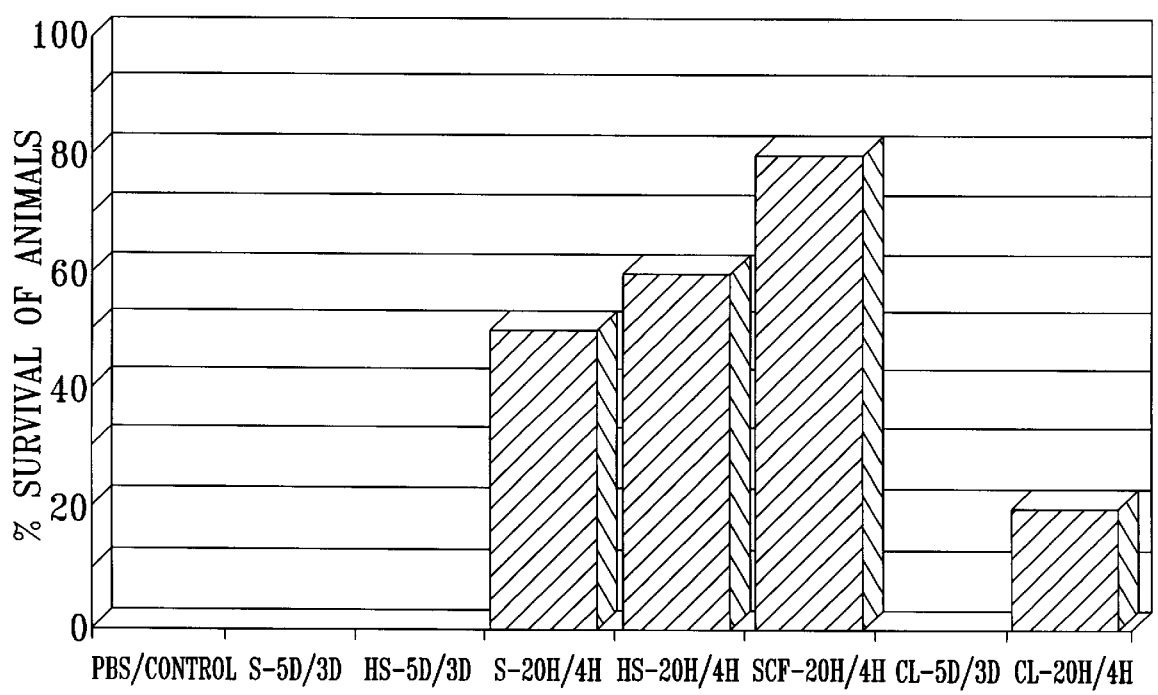
FIG. 3 is a graph showing the survival of mice exposed to 800 cGy irradiation, with various protective measures including the lyophilized shark liver extract.
Figure 3:
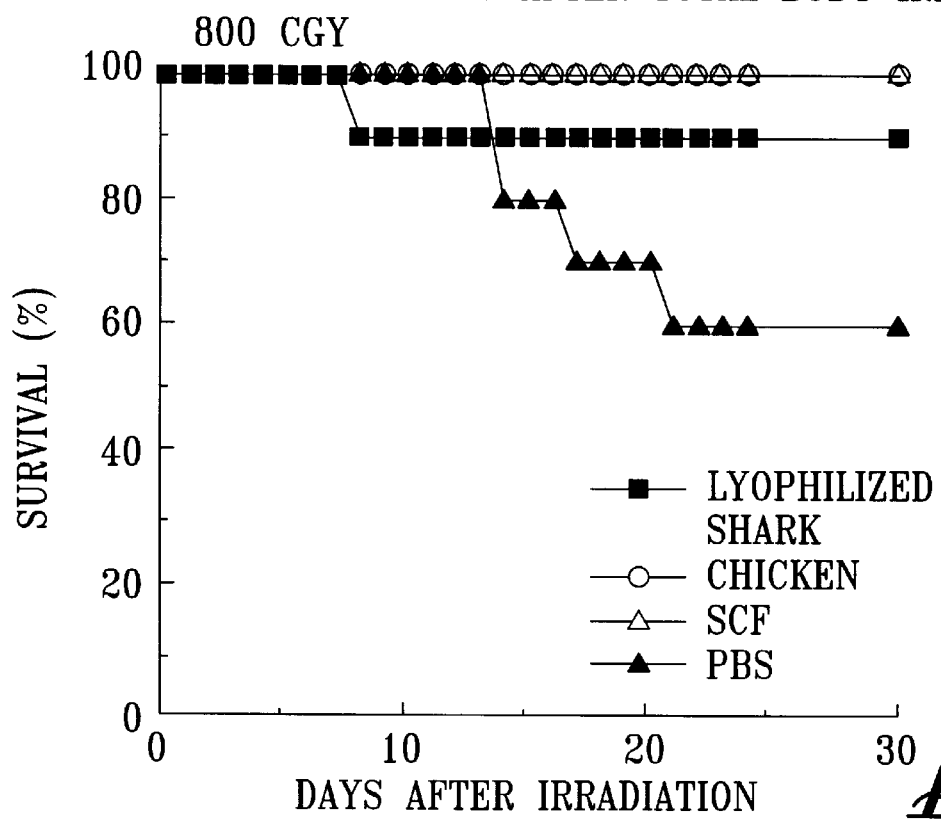
Figure 4:
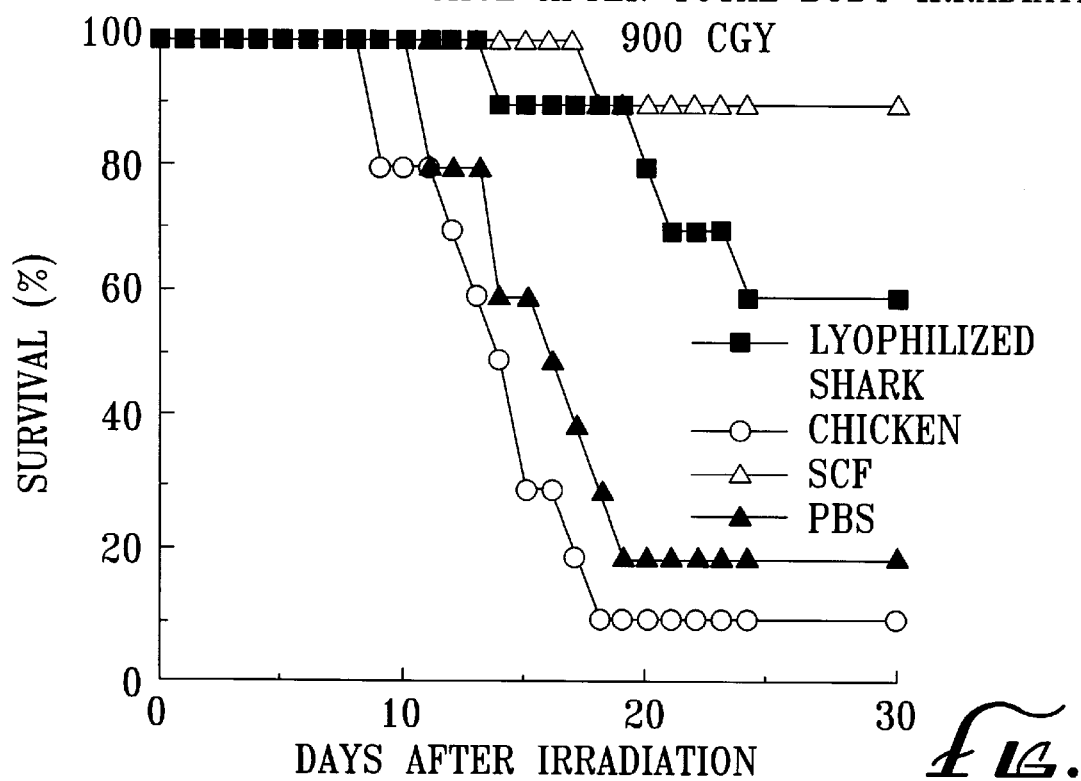
FIG. 4 is a graph showing the survival of mice exposed to 900 cGy irradiation with various protective measures including the lyophilized shark liver extract.

FIGS. 2–5 are graphical representations of the results obtained. In a first instance (FIG. 2), two differently treated shark liver extracts are compared with controls in mice irradiated at 900 cGy. In each instance, the extract or controls were reconstituted to the original (prelypholized) concentration and 0.2 ml were administered to the mice intraperitoneal or subcutaneously at 20 and 4 hours prior to radiation exposure. FIGS. 3 and 4 compare the effect of lyophilized shark liver extract when the mice are exposed to 800 or 900 cGy under the same protocol. FIG. 5 is a bar chart comparing the survival rate of mice exposed to 900 cGy after treatment with the shark liver extract(S), heated shark liver extract (HS), PBS, SCF and chicken liver extract (CL) under two different delivery regimes for the extract, namely 5 days and 3 days prior to radiation (5 d/3 d) or 20 hours and 4 hours prior to radiation (20 h/4 h). While the SCF results in an 80% survival rate at the 20h/4h, the shark liver extract, with or without heating, shows a survival rate of 50% and 60% which is significantly greater than the PBS control or chicken liver extract.

Table 1 shows the effect of Shark Liver Extract (0.2 ml) on stimulating NK cell activities in mice.

TABLE 1

EFFECT OF HAWAIIAN WHITE-TIPPED SHARK LIVER EXTRACT TREATMENT ON NK CELL ACTIVITY OF MICE
% CYTOTOXICITY, EFFECTOR: TARGET RATIO

| SPLEEN °CELLS | TREATMENT WITH LIVER EXTRACT | 200:1 | 100:1 | 50:1 | 25:1 |
|---|---|---|---|---|---|
| Normal | — | 28.8 | 18.3 | 16.0 | 8.3 |
| Extract Treated | 0.2 ml | 52.2 | 46.3 | 25.7 | 13.7 |
| Extract treated | 0.1 ml | 34.8 | 21.8 | 10.7 | 8.5 |

To generate this data, °C.57BL/6 mice were inoculated i.p. with 0.1 and 0.2 ml of shark liver extract. Two days later, spleens of these mice were harvested and simple cell suspensions were prepared and the NK cell activity was tested against $^{51}$Cr-labeled YAC-1 lymphoma cells. The extract contained 22 mg of protein per ml.

Results of this assay show that treatment of mice with 0.2 ml of shark liver extract resulted in substantial stimulation of NK cell activity. Treatment with 0.1 ml of the extract was not sufficient to significantly increase NK cell activity of the treated mice indicating a dose responsive relationship in the ability of SLE to stimulate immune response in NK cells carrying the $^{51}$Cr labeled YAC-1 lymphoma cells.

Based on the animal studies, it is believed that the solubilized lyophilized form of the shark liver extract can be incorporated into a standardized rectal suppository form which, upon placement within the required pretreatment time period, would confer radiation protection to the rectal/pelvic region during the course of radiation therapy for stage BII or C prostatic carcinoma without altering the expected response of the malignant tissue within the prostate gland to a delivered dose of radiation, thus diminishing the chance of radiation produced cystitis or proctitis developing. Typical carriers used in standardized rectal suppositories include beeswax/glycerol. The proper treatment protocol is based on the test results in animals of radiation protection when given 20 hours and 4 hours before delivery of high dose radiation. The 800 and 900 cGy studies suggest that higher dosage of radiation with better tumor eradication could be achieved with fewer side effects by this method. Secondly, using lyophilized shark liver extract delivered prior to, during, and following courses of treatment for advanced prostate cancer with the chemotherapeutic agent Suramin, patients with hormonally unresponsive advanced carcinoma of the prostate and who have documented rising levels of PSA after having undergone MAB (maximum androgen blockade), that is patients who have undergone orchiectomy and are on Flutamide or are on LH/RH inhibitors with Flutamide, will show improved treatment effects and reduced side effects from the chemotherapy treatment when compared to those not receiving SLE or receiving a placebo treatment.

Although the present invention has been described in considerable detail with reference to certain preferred versions and uses thereof, other versions and uses are possible. For example, while Hawaiian white-tipped shark liver was used, other types of shark liver can be used, and it is not believed that the specific type of shark used will give a different effect. Other suitable shark species include juvenile nurse sharks, horned shark, lemon shark, tiger shark, mako, black tip and sand sharks. However, deep sea sharks are preferred as they are believed to have less environmental toxins than bottom feeding or scavenger sharks. Similar effects may be obtained from the livers of skates and rays which occupy the same taxonomic subclass, called elastobranchs. Further, instead of using water in the above procedures, a saline or physiological solution is believed to be a suitable replacement. The lyophilization product prepared as described above has been shown to have a longer shelf life (i.e., up to 6 months) and to be more consistent in the results obtain than any of the other biological products derive from sharks discussed above.

Further, while use of the shark liver extract embodying features of the invention was described for use in the treatment of prostate cancer using radiation, it would be recognized that the invention has benefit for use in conjunction with other cancer treatments, for treating other cancers, or for use in disease states resulting from a compromised immune system. Also, while the process is directed to recovering a water soluble shark liver extract, the other layers separated by the centrifuge, particularly the oil layer, can be processed in a similar manner to provide a dry non-water soluble shark liver extract. Therefore, the spirit and scope of the appended claims should not be limited to the description of the preferred versions contained herein.

What is claimed is:

1. A process for preparing a purified biological material capable of stimulating the immune system of mammals and reducing the deleterious effect on non-cancerous cells resulting from the administration of radiation treatment comprising the steps of:
   a) cooling shark liver to about 0° C.,
   b) pulverizing said cooled shark liver to produce a finely ground material,
   c) mixing the finely ground material with an equal amount, by weight, of water while maintaining the mixture at about 0° C. and stirring said mixture for about 20 minutes,
   d) centrifuging the mixture at 0° C. to 4° C. for 4 to 6 hours until said mixture separates into three distinct layers, said layers comprising a cellular layer, an aqueous layer and an oil layer,
   e) separating the aqueous layer from the other layers,
   f) filtering the aqueous layer to generate a filtered solution; and
   g) spraying the filtered solution into a vacuum chamber held at 0° C. to 4° C. to produce a dry powdered substance for pharmaceutical administration.

2. The process of claim 1 including the step of removing colored material from the aqueous layer following separation thereof from the other layers by eluting said aqueous layer through a resin.

3. A method for reducing the deleterious effect of radiation treatment on non-cancerous cells resulting from the administration of radiation treatment to a mammal comprising the steps of:
   a) cooling shark liver to about 0° C.,
   b) granulating said cooled shark liver to produce a finely ground powder,
   c) mixing the finely ground powder with an equal amount, by weight, of water while maintaining the mixture at about 0° C. and stirring said mixture for about 20 minutes,
   d) centrifuging the mixture at 0° C. to 4° C. for 4 to 6 hours until said mixture separates into three distinct layers, said layers comprising a cellular layer, an aqueous layer and an oil layer,
   e) separating the aqueous layer from the other layers,
   f) filtering the aqueous layer to generate a filtered solution,
   g) spraying the filtered solution into a vacuum chamber held at 0° C. to 4° C. to produce a dry powdered product,
   h) mixing said dry powdered product with a physiologically acceptable carrier to produce a pharmaceutical composition; and
   i) administering said composition to the body within at least 20 hours prior to administering said radiation treatment to a mammal.

4. The method of claim 3 wherein the composition is a suppository for transrectal or transurethral delivery comprising the dry powdered product in combination with a physiologically acceptable solid carrier that is meltable at mammalian body temperature.

5. The method of claim 3 wherein the composition is a liquid for administration to a mammal by transcutaneous, intravenous, intramuscular or oral delivery, said liquid comprising the dry powdered product dissolved in a physiologically acceptable solution.

6. The method of claim 3 wherein the composition is a coated gel capsule suitable for enteric administration.

* * * * *